United States Patent [19]

Clayton et al.

[11] 4,385,060
[45] May 24, 1983

[54] PENICILLINS

[75] Inventors: John P. Clayton, Horsham; Martin Cole, Dorking, both of England

[73] Assignee: Beecham Group Limited, England

[21] Appl. No.: 189,622

[22] Filed: Sep. 22, 1980

[30] Foreign Application Priority Data

Oct. 2, 1979 [GB] United Kingdom ................ 7934062

[51] Int. Cl.³ ..................... A61K 31/43; C07D 499/56
[52] U.S. Cl. .................................... 424/271; 260/239.1
[58] Field of Search ...................... 260/239.1; 424/271

[56] References Cited

U.S. PATENT DOCUMENTS 3,853,849 12/1974 Hardy et al. ..................... 260/239.1
4,171,303 10/1979 Huhn et al. ...................... 260/239.1

FOREIGN PATENT DOCUMENTS 1229670 4/1971 United Kingdom .
1304202 1/1973 United Kingdom .
1455529 11/1976 United Kingdom .
2005538 4/1979 United Kingdom .

Primary Examiner—Glennon H. Hollrah
Assistant Examiner—Vera C. Clarke

Attorney, Agent, or Firm—Jacobs & Jacobs

[57] ABSTRACT

6β-[2-(2'-methylphenoxycarbonyl)-2-thien-3'-ylacetamido] penicillanic acid of formula (II):

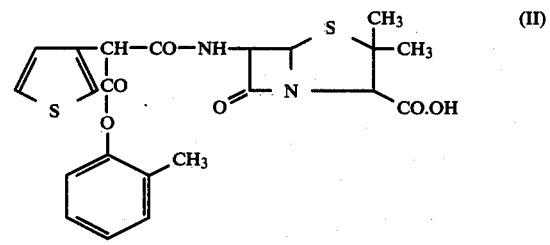

and pharmaceutically acceptable salts and in vivo hydrolyzable esters thereof, are active against Gram-positive and Gram-negative bacteria which makes them useful as therapeutic and prophylactic agents against bacterial infections in animals, including man and poultry. A process for the preparation and pharamceutical compositions comprising the penicillin, are also described.

8 Claims, No Drawings

PENICILLINS

This invention relates to penicillins, and more particularly to the o-tolyl ester of an α-carboxy penicillin.

The penicillin and its salts are active against Gram-positive and Gram-negative bacteria which makes them useful as therapeutic and prophylactic agents against bacterial infections in animals, including man and poultry.

U.S. Pat. No. 3,853,849 claims a penicillin mono-ester of the formula (I):

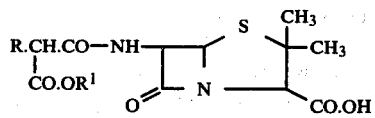

or a non-toxic pharmaceutically acceptable salt thereof, wherein R is phenyl, or 3-thienyl and $R^1$ is phenyl or methylphenyl. That patent specifically discloses the compound wherein R is 3-thienyl and $R^1$ is phenyl, ie the α-phenyl ester of α-carboxy-3-thienylmethyl penicillin.

Such mono-esters have the advantage that they are orally absorbed in animal species, including man, where they undergo in vivo hydrolysis to produce a degree of blood level antibiotic activity due to the free α-carboxy-penicillin that is not attained when the α-carboxy-penicillin itself is orally administered to the animal species.

British Pat. No. 1,455,529 claims specifically the α-para-tolyl mono-ester of α-carboxy-3-thienylmethyl penicillin which demonstrates a high degree of oral absorption in man.

The present invention is based on the discovery that the α-ortho-tolyl ester of α-carboxy-3-thienylmethyl penicillin exhibits considerably higher bioavailability after oral administration in man than either the phenyl or the p-tolyl esters. Although the p-tolyl ester is somewhat better absorbed than the phenyl ester, this improvement is only of the order of 15% at the peak serum level. In contrast, we have now found that the o-tolyl ester produces peak serum levels in man of the order of 150% higher than those produced by the phenyl ester, and the bioavailability as measured by the AUC (area under curve) method for the o-tolyl ester is about 120–220% higher than for the phenyl ester (ie 2–3 times as efficiently absorbed). These dramatic differences could not have been predicted from a knowledge of the esters disclosed in U.S. Pat. No. 3,853,849 and U.K. Pat. No. 1,455,529.

Accordingly, this invention provides 6β-[2-(2'-methylphenoxycarbonyl)-2-thien-3'-ylacetamido]-penicillanic acid of formula (II):

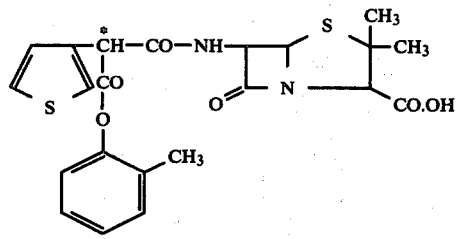

or a pharmaceutically acceptable salt or in vivo hydrolysable ester thereof.

The compounds of the present invention include the pharmaceutically acceptable esters of the 3-carboxylic acid group which hydrolyse readily in the human body to produce the parent acid, for example acyloxyalkyl groups such as acetoxymethyl, pivaloyloxymethyl, α-acetoxyethyl, α-acetoxybenzyl and α-pivaloyloxyethyl groups; alkoxycarbonyloxyalkyl groups, such as ethoxycarbonyloxymethyl and α-ethoxycarbonyloxyethyl; dialkylaminoalkyl groups such as dimethylaminomethyl, dimethylaminoethyl, diethylaminomethyl or diethylaminoethyl; and lactone groups such as phthalidyl or dimethoxyphthalidyl.

Suitable salts of the 3-carboxylic acid group of the compound of formula (I) include metal salts, eg aluminium, alkali metal salts such as sodium or potassium, alkaline earth metal salts such as calcium or magnesium, and ammonium or substituted ammonium salts, for example those with lower alkylamino such as triethylamine, hydroxy-lower alkylamines such as 2-hydroxyethylamine, bis-(2-hydroxyethyl)-amine or tri-(2-hydroxyethyl)-amine, cycloalkylamines such as bicyclohexylamine, or with procaine, dibenzylamine, N,N-dibenzylethylenediamine, 1-ephenamine, N-ethylpiperidine, N-benzyl-β-phenethylamine, dehydroabeitylamine, N,N'-bisdehydroabietylethylenediamine, or bases of the pyridine type such as pyridine, collidine or quinoline, or other amines which have been used to form salts with known penicillins.

The carbon atom marked * in formula (I) is asymmetric. This invention includes both optically active isomers at that position as well as the D,L-mixture.

The compounds of formula (II) may be prepared by reacting a compound of formula (III):

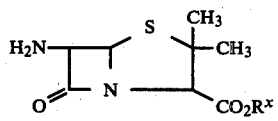

wherein the amino group is optionally substituted with a removable group which permits acylation to take place and wherein $R^x$ is hydrogen or a carboxyl blocking group; with an N-acylating derivative of an acid of formula (IV):

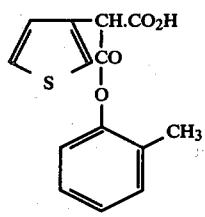

and thereafter if necessary carrying out one or more of the following steps:
(i) removal of any substituent on the amide group;
(ii) removal of any carboxyl blocking group $R^x$;
(iii) converting the product to a salt or in vivo hydrolysable ester thereof.

Suitable groups which permit acylation to take place and which are optionally present on the amino group of the starting material of the formula (III) include N-silyl, N-stannyl and N-phosphorus groups, for example trialkylsilyl groups such as trimethylsilyl, trialkyltin groups such as tri-n-butyltin, groups of formula —P.R$^a$R$^b$ wherein R$^a$ is an alkyl, haloalkyl, aryl, aralkyl, alkoxy, haloalkoxy, aryloxy, aralkyloxy or dialkylamino group, R$^b$ is the same as R$^a$ or is halogen or R$^a$ and R$^b$ together form a ring; suitable such phosphorus groups being —P(OC$_2$H$_5$)$_2$, —P(C$_2$H$_5$)$_2$,

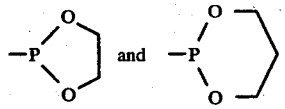

Suitable carboxyl-blocking derivatives for the group —CO$_2$R$^x$ in formula (II) include salts, ester, and anhydride derivatives of the carboxylic acid. The derivative is preferably one which may readily be cleaved at a later stage of the reaction. Suitable salts include inorganic salts, for example alkali metal salts such as the sodium salt, tertiary amine salts, such as those with tri-lower-alkylamines, N-ethylpiperidine, 2,6-lutidine, pyridine, N-methylpyrrolidine, dimethylpiperazine. A preferred salt is with triethylamine.

Suitable ester-forming carboxyl-blocking groups are those which may be removed under conventional conditions. Such groups for R$^x$ include benzyl, p-methoxybenzyl, 2,4,6-trimethylbenzyl, 3,5-di-t-butyl-4-hydroxybenzyl, benzoylmethyl, p-nitrobenzyl, 4-pyridylmethyl, 2,2,2-trichloroethyl, 2,2,2-tribromoethyl, t-butyl, t-amyl, diphenylmethyl, triphenylmethyl, adamatyl, 2-benzyloxyphenyl, 4-methylthiophenyl, tetrahydrofur-2-yl, tetrahydropyran-2-yl, pentachlorophenyl, p-toluenesulphonylethyl, methoxymethyl, a silyl, stannyl or phosphorus-containing group, such as described above, an oxime radical of formula —N=CHR° where R° is aryl or heterocyclic, or an in vivo hydrolysable ester radical such as defined above.

The carboxyl group may be regenerated from any of the above esters by usual methods appropriate to the particular R$^x$ group, for example, acid- and base- catalysed hydrolysis, or by enzymically-catalysed hydrolysis, or by hydrogenation. The hydrolysis must of course be carried out under conditions to which the ortho-tolyl ester group in the side-chain is stable.

A reactive N-acylating derivative of the acid (IV) is employed in the above process. Suitable N-acylatinng derivatives include an acid halide, preferably the acid chloride or bromide. Acylation with an acid halide may be affected in the presence of an acid binding agent for example tertiary amine (such as triethylamine or dimethylaniline), an inorganic base (such as calcium carbonate or sodium bicarbonate) or an oxirane, which binds hydrogen halide liberated in the acylation reaction. The oxirane is preferably a (C$_{1-6}$)-1,2-alkylene oxide—such as ethylene oxide or propylene oxide. The acylation reaction using an acid halide may be carried out at a temperature in the range −50° C. to +50° C., preferably −20° C. to +20° C., in aqueous or non-aqueous media such as aqueous acetone, ethyl acetate, dimethylacetamide, dimethylformamide, acetonitrile, dichloromethane, 1,2-dichloroethane, or mixtures thereof. Alternatively, the reaction may be carried out in an unstable emulsion of water-immiscible solvent, expecially an aliphatic ester or ketone, such as methyl isobutyl ketone or butyl acetate.

The acid halide may be prepared by reacting the acid (IV) or a salt thereof with a halogenating (eg chlorinating or brominating) agent such as phosphorus pentachloride, thionyl chloride or oxalyl chloride.

Alternatively, the N-acylating derivative of the acid (IV) may be symmetrical or mixed anhydride. Suitable mixed anhydrides are alkoxyformic anhydrides, or anhydrides with, for example carbonic acid monoesters, trimethyl acetic acid, thioacetic acid, diphenylacetic acid, benzoic acid, phosphorus acids (such as phosphoric or phosphorous acids), sulphuric acid or aliphatic or aromatic sulphonic acids (such as p-toluenesulphonic acid). The mixed or symmetrical anhydrides may be generated using N-ethoxycarbonyl-2-ethoxy-1,2-dihydroquinoline. When a symmetrical anhydride is employed, the reaction may be carried out in the presence of 2,4-lutidine as catalyst.

Alternative N-acylating derivatives of acid (IV) are the acid azide, or activated esters such as esters with 2-mercaptopyridine, cyanomethanol, p-nitrophenol, 2,4-dinitrophenol, thioalcohols such as thiophenol, methanethiol, ethanethiol and propanethiol, halophenols, including pentachlorophenol, monomethoxyphenol or 8-hydroxyquionline, N-hydroxysuccinimide or 1-hydroxybenztriazole; or amides such as N-acylsaccharins or N-acylphthalimides; or an alkylidine iminoester prepared by reaction of the acid (IV) with an oxime.

Other reactive N-acylating derivatives of the acid (IV) include the reactive intermediate formed by reaction in situ with a condensing agent such as a carbodiimide, for example N,N-diethyl-, dipropyl- or diisopropylcarbodiimide, N,N'-di-cyclohexylcarbodiimide, or N-ethyl-N'-γ-dimethylaminopropylcarbodiimide; a suitable carbonyl compound, for example N,N'-carbonyldiimidazole or N,N'-carbonylditriazole; an isoxasolinium salt, for example N-ethyl-5-phenylisoxazolinium-3-sulphonate or N-t-butyl-5-methylisoxazolinium perchlorate; or an N-alkoxycarbonyl-2-alkoxy-1,2-dihydroquinoline, such as N-ethoxycarbonyl-2-ethoxy-1,2-dihydroquinoline. Other condensing agents include Lewis acids (for example BBr$_3$—C$_6$H$_6$); or a phosphoric acid condensing agent such as diethylphosphorylcyanide. The condensation reaction is preferably carried out in an organic reaction medium, for example methylene chloride, dimethylformamide, acetonitrile, alcohol, benzene, dioxan or tetrahydrofuran.

Compounds of formula (II) may also be prepared by reacting a compound of formula (V):

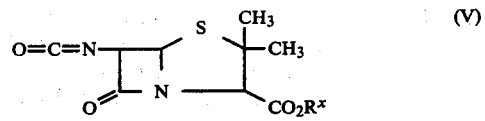

wherein R$^x$ is as defined above with respect to formula (III) above; with an acid of formula (IV) or a carbanion of formula (IVA):

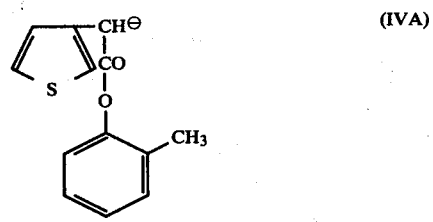

and thereafter if necessary carrying out one or more of the following steps:
  (i) removal of any carboxyl blocking group $R^x$;
  (ii) converting the product to a salt or in vivo hydrolysable ester thereof.

This reaction is preferably carried out at a temperature in the range $-10°$ to $+50°$ C. in an inert organic solvent, such as methylene dichloride, in the presence of a basic catalyst such as triethylamine, pyridine or a nitrogen-containing aromatic mono- or bi-cyclic compound such as 4-methoxy-(dimethylamino)pyridine, 1-methyl(benz)imidazole or imidazo[1,2-α]pyridine.

A third method of preparation of the compounds of formula (II) comprises:
  (a) treating a compound of formula (VI):

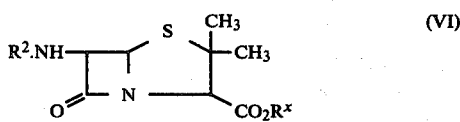
(VI)

wherein $R^x$ is a carboxyl-blocking group, and $R^2$ is an acyl group, in particular an acyl group derived from the side-chain of a natural penicillin, such as benzyl penicillin or phenoxymethyl penicillin; with an agent forming an imino halide;
  (b) treating the imino halide with a compound to introduce a group $QR_f$ on the imino carbon atom, wherein Q is oxygen, sulphur or nitrogen and $R_f$ is an alkyl group of from 5 to 14 carbon atoms, to form an iminoether, iminothioether, or amidine (when Q is O, S, or N respectively);
  (c) reacting with an N-acylating derivative of an acid of formula (IV) above;
  (d) treating with water; and
  (e) optionally removing the carboxyl-blocking group $R^x$.

A suitable agent for preparing an imino halide is an acid halide in the presence of an acid binding agent such as a tertiary amine, eg pyridine, triethylamine, or N,N-dimethylaniline. Examples of suitable acid halides are phosphorus pentachloride, phosgene, phosphorous pentabromide, phosphorus oxychloride, oxalyl chloride and p-toluene sulphonic acid chloride. Phosphorus pentachloride and phosphorus oxychloride are preferred. The reaction may be conducted under cooling, preferably at temperatures from $0°$ C. to $-30°$ C. when phosphorus pentachloride is employed. The amount of the tertiary amine is preferably 3-5 mols per mol of phosphorus pentachloride. It is also preferable to use the phosphorus halide in an amount slightly in excess of that of the starting material.

The resulting imino compounds are then treated to introduce a $-QR_f$ group onto the imino carbon atom. This is preferably effected by reacting the imino halide with a corresponding alcohol. Examples of suitable alcohols for reaction with the imino halide are aliphatic alcohols containing from 1 to 12 carbon atoms, preferably 1 to 5 carbon atoms, such as methanol, ethanol, propanol, isopropyl alcohol, amyl alcohol and butyl alcohol, and aralkyl alcohols such as benzyl alcohol and 2-phenylethanol.

The reaction of the alcohol with the imino halide is preferably effected in the presence of an acid binding agent, such as a tertiary amine, preferably pyridine, and the reaction is usually carried out without isolating the imino halide from the reaction mixture.

Thereafter the imino compound is caused to react with an N-acylating derivative of an acid of formula (IV). The comments made above concerning such N-acylating derivatives, and the conditions for carrying out acylations also apply in this case. In particular, the presence of a tertiary amine such as pyridine or N,N-dimethylaniline in the reaction system is preferred.

Finally, the product is treated with water. The water treatment may be conducted together with the isolation of the desired material. That is the reaction mixture may be added to water or a saturated aqueous solution of sodium chloride and then the aqueous layer formed is separated from the organic solvent layer.

The compounds of formula (II) may also be prepared by esterification of a compound of formula (VII) or a salt thereof:

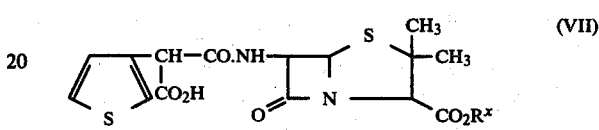
(VII)

wherein $R^x$ is hydrogen or a carboxyl blocking group; with compound of formula (VIII):

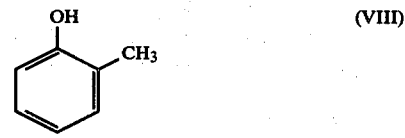
(VIII)

and thereafter if necessary carrying out one or more of the following steps:
  (i) removal of any carboxyl blocking groups $R^x$;
  (ii) converting the product to a salt or in vivo hydrolysable ester thereof.

Esterification may be performed by any conventional method, for example by reaction of the free acid with a compound of formula (VIII) in the presence of a catalyst or by reaction of a salt of the free acid:
  (a) with the appropriate halide or sulphate derivative of the compound of formula (VIII) in the presence of dimethylsulphoxide and calcium carbonate or with the halide in the presence of hexamethyl phosphoramide; or
  (b) by phase transfer catalysis methods with the halide and/or sulphate of the alcohol in aqueous and/or organic solution in the presence of a quaternary ammonium salt such as tetrabutyl ammonium bisulphate or halide, or benzyltrimethylammonium halide.

Alternatively, the mixed anhydride derivative of the compound of formula (VII) may be reacted with the compound of formula (VIII) or an alkali metal or alkaline earth metal salt thereof. Suitable salts include the lithium, sodium or magnesium salts. Suitable mixed anhydrides are alkoxyformic anhydrides, or anhydrides with, for example trimethyl acetic acid, thioacetic acid, diphenylacetic acid, benzoic acid, phosphorus acids (such as phosphoric or phosphorous acids), sulphuric acid or aliphatic or aromatic sulphonic acids (such as p-toluenesulphonic acid). The mixed anhydride may be generated in situ. For example, using isobutyl chloroformate or ethyl chloroformate.

Other reactive esterifying derivatives of the acid (VII) include the reactive intermediate formed by reaction in situ with a condensing agent such as a carbodiimide, for example N,N-diethyl-, dipropyl- or diisopropylcarbodiimide, N,N'-di-cyclohexylcarbodiimide, or N-ethyl-N'-γ-dimethylaminopropylcarbodiimide; a suitable carbonyl compound, for example N,N'-carbonyldiimidazole or N,N'-carbonylditriazole; an isoxasolinium salt, for example N-ethyl-5-phenylisoxazolinium-3-sulphonate or N-t-butyl-5-methylisoxazolinium perchlorate; or an N-alkoxycarbonyl-2-alkoxy-1,2-dihydroquinoline, such as N-ethoxycarbonyl-2-ethoxy-1,2-dihydroquinoline. Other condensing agents include Lewis acids (for example BBr$_3$—C$_6$H$_6$); or a phosphoric acid condensing agent such as diethylphosphorylcyanide. The condensation reaction is preferably carried out in an organic reaction medium, for example methylene chloride, dimethylformamide, acetonitrile, alcohol, benzene, dioxan or tetrahydrofuran.

The antibiotic compounds according to the invention may be formulated for administration in any convenient way for use in human or veterinary medicine, by analogy with other antibiotics, and the invention therefore includes within its scope a pharmaceutical composition comprising a compound of formula (I) above together with a pharmaceutical carrier or excipient.

The compositions may be formulated for administration by any route, although an oral administration is preferred. The compositions may be in the form of tablets, capsules, powders, granules, lozenges, or liquid preparations, such as oral or sterile parenteral solutions or suspensions.

Tablets and capsules for oral administration may be in unit dose presentation form, and may contain conventional excipients such as binding agents for example syrup, acacia, gelatin, sorbitol, tragacanth, or polyvinyl-pyrollidone; fillers, for example lactose, sugar, maize-starch, calcium phosphate, sorbitol or glycine; tabletting lubricants, for example magnesium stearate, talc, polyethylene glycol or silica; disintegrants, for example potato starch; or acceptable wetting agents such as sodium lauryl sulphate. The tablets may be coated according to methods well known in normal pharmaceutical practice. Oral liquid preparations may be in the form of, for example, aqueous or oily suspensions, solutions, emulsions, syrups, or elixirs, or may be presented as a dry product for reconstitution with water or other suitable vehicle before use. Such liquid preparations may contain conventional additives such as suspending agents, for example sorbitol, syrup, methyl cellulose, glucose syrup, gelatin, hydroxyethylcellulose, carboxymethyl cellulose, aluminium stearate gel or hydrogenated edible fats, emulsifying agents, for example lecithin, sorbitan monooleate, or acacia; non-aqueous vehicles (which may include edible oils), for example almond oil, fractionated coconut oil, oily esters such as glycerine, propylene glycol, or ethyl alcohol; preservatives, for example methyl or propyl p-hydroxybenzoate or sorbic acid, and if desired convention flavouring or colouring agents.

Suppositories will contain conventional suppository bases, eg cocao-butter or other glyceride.

For parenteral administration, fluid unit dosage forms are prepared utilizing the compound and a sterile vehicle, water being preferred. The compound, depending on the vehicle and concentration used, can be either suspended or dissolved in the vehicle. In preparing solutions the compound can be dissolved in water for injection and filter sterilized before filling into a suitable vial or ampoule and sealing. Advantageously, adjuvants such as local anaesthetic, preservative and buffering agents can be dissolved in the vehicle. To enhance the stability, the composition can be frozen after filling into the vial and the water removed under vacuum. The dry lyophilized powder is then sealed in the vial and an accompanying vial of water for injection is supplied to reconstitute the liquid prior to use. Parenteral suspensions are prepared in substantially the same manner except that the compound is suspended in the vehicle instead of being dissolved and sterilization cannot be accomplished by filtration. The compound can be sterilized by exposure to ethylene oxide before suspending in the sterile vehicle. Advantageously, a surfactant or wetting agent is included in the composition to facilitate uniform distribution of the compound.

The compositions may contain from 0.1% to 99% by weight, preferably from 10% to 60% by weight, of the active material, depending on the method of administration. Where the compositions comprise dosage units, each unit will preferably contain from 50 to 500 mg, of the active ingredient. The dosage as employed for adult human treatment will preferably range from 100 to 3000 mg, per day, for instance 1500 mg, per day, depending on the route and frequency of administration.

The compound of formula (I) may be the sole therapeutic agent in the compositions of the invention or a combination with other antibiotics may be employed. Advantageously the compositions also comprise a compound of formula (IX) or a pharmaceutically acceptable salt or ester thereof:

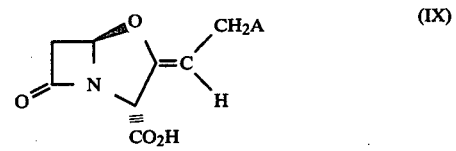

wherein A is hydroxyl, substituted hydroxyl, thiol, substituted thiol, amino, mono- or di-hydrocarbylsubstituted amino, or mono- or di-acylamino.

Preferably, A is hydroxyl, i.e. the compound of formula (IX) is clavulanic acid or a pharmaceutically acceptable salt thereof, in particular an alkali metal salt.

It has been stated that the penicillin α-ester of formula (II), although covered generically by the claims of U.S. Pat. No. 3,853,849, is considerably and unpredictably superior to the remaining esters claimed in that patent. To support this statement, table 1 shows the serum concentration, the area under curve, and urinary excretion of α-carboxy-3-thienylmethylpenicillin (hereinafter called ticarcillin) produced when the phenyl, and o-tolyl esters of ticarcillin were administered orally to a panel of human volunteers, in four separate experiments, referred to as A–D.

To obtain the results shown in table 1, the two esters of ticarcillin were each given to a panel of fasting human volunteers in a syrup formulation in an amount equivalent to provide either 200 or 400 mg (as stated in table 1) of the free ticarcillin after the expected in vivo hydrolysis. Periodic blood samples were taken from the volunteers and each assayed for ticarcillin content by a standard bio-assay technique. The urine excreted by each volunteer within the 6 hours following administration was also collected and assayed for the free ticarcillin. All three parameters (viz the urinary excretion level, the peak serum concentration achieved and the total area under the curve when the serum concentration is plotted against time) are indications of the minimum degree to which the penicillin ester has been absorbed after oral administration and then hydrolysed in vivo. After oral administration of the two esters of ticarcillin, analysis of blood and urine samples showed that very little of the esters was present in the blood stream (<0.2 μg/m) or urine (ca 1% of dose for the phenyl ester, and ca 2% of dose for the o-tolyl ester). Therefore, it is valid to talk of the absorption of these esters in terms of ticarcillin in the blood stream and urine.

The results achieved were as follows:

TABLE 1

| α-Ester of ticarcillin | Mean serum concentration (μg/ml) of ticarcillin | | | | | | | AUC (μg min ml$^{-1}$) | urinary excretion 0–6 h (% of dose) |
|---|---|---|---|---|---|---|---|---|---|
| | 15 m | 30 m | 45 m | 1 h | 1.5h | 2 h | 4 h | | |
| Experiment A - oral dose equivalent to 200 mg ticarcillin | | | | | | | | | |
| phenyl | 1.62 | 2.88 | 2.34 | 1.92 | 1.30 | 1.10 | <0.4 | 253.65 | 15.14 |
| o-tolyl | 3.77 | 6.80 | 6.98 | 6.20 | 4.93 | 3.82 | <0.4 | 808.75 | 39.26 |
| Experiment B - oral dose equivalent to 200 mg ticarcillin | | | | | | | | | |
| phenyl | 1.35 | 2.73 | 2.67 | 2.45 | 1.45 | 0.82 | <0.8 | 343.50 | 22.46 |
| o-tolyl | 4.22 | 7.85 | 6.73 | 5.20 | 3.58 | 3.25 | <0.8 | 1103.30 | 41.74 |
| Experiment C - oral dose equivalent to 400 mg ticarcillin | | | | | | | | | |
| phenyl | 2.7 | 6.7 | 7.3 | 5.8 | 4.3 | 2.4 | <0.8 | 686.7 | 23.7 |
| o-tolyl | 4.8 | 11.7 | 11.1 | 9.5 | 8.2 | 6.5 | 1.4 | 1520.9 | 36.4 |
| Experiment D - oral dose equivalent to 400 mg ticarcillin | | | | | | | | | |
| phenyl | 1.4 | 6.0 | 5.1 | 4.6 | 3.8 | 2.6 | <0.8 | 599.5 | 21.7 |
| o-tolyl | 5.7 | 10.6 | 12.6 | 10.8 | 8.3 | 5.7 | 0.8 | 1428.8 | 39.0 |

AUC = Area under curve

The results in table 1 demonstrate that the bioavailability of ticarcillin after oral administration of the α-ortho-tolyl ester is considerably greater than after administration of the phenyl ester. The parameter which can be most directly compared to show this difference is the area under curve (AUC). Table 2 shows the percentage increase in the AUC for the ortho-tolyl ester compared to the phenyl ester, calculated from the data in table 1.

TABLE 2

| Experiment | % increase in AUC |
|---|---|
| A | 219% |
| B | 223% |
| C | 121% |
| D | 138% |

It can be seen from Table 2 that the bioavailability of ticarcillin, measured by AUC, after oral administration of the α-ortho-tolyl ester is some two- to three-fold greater than that after administration of the α-phenyl ester. This conclusion is confirmed by the greater urinary recovery of ticarcillin detected after administration of the α-ortho-tolyl ester.

The improved bioavailability can also be seen from the individual mean serum concentration figures in table 1. In contrast the α-para-tolyl ester disclosed in British Pat. No. 1,455,529 is much less well absorbed than the α-ortho-phenyl ester. This can be seen by the comparison with the phenyl ester and for convenience the data from specification No. 1,455,529 is repeated in table 3 below:

TABLE 3

(Administration as syrup containing equivalent of 400 mg ticarcillin)

| Monoester group | Mean serum concentration (μg/ml) | | | | | | Peak serum concentration (μg/ml) | Urinary excretion 0–6 h (%) |
|---|---|---|---|---|---|---|---|---|
| | 20 m | 40 m | 1 h | 1.5 h | 2 h | 3 h | | |
| phenyl | 5.4 | 7.5 | 5.2 | 3.6 | 2.4 | <1.6 | 7.5 | 23 |
| p-tolyl | 5.9 | 8.6 | 6.8 | 4.9 | 3.7 | <1.6 | 8.6 | 30 |

Although the p-tolyl ester is absorbed to a greater extent than the phenyl ester, the difference is small compared to the dramatic improvement seen with the ortho-tolyl ester. The percentage increase of the peak serum levels of the p-tolyl compared to the phenyl ester is only 14.7%. In fact the differences in mean serum concentrations in table 3 are not statistically significant.

The following Examples illustrate this invention.

EXAMPLE 1

Sodium 6,β-[2-(2'-methylphenoxycarbonyl)-2-thien-3'-ylacetamido]penicillanate

2-Methylphenyl hydrogen thien-3-ylmalonate (110.0 g, 0.40 mole), dimethylformamide (1.0 ml) and thionyl chloride (29.2 ml, 48.8 g, 0.41 mole) in dichloromethane (880 ml) were heated under reflux for 1.5 hours then evaporated to dryness in vacuo at <30° to give 2-(2-methylphenoxycarbonyl)-2-thien-3'-ylacetyl chloride.

This acid chloride in acetone (200 ml) was cooled to −17°±2° then added to a suspension, prepared from 6-APA (90.8 g, 0.42 mole) in water (320 ml) cooled to 10° adjusted to pH 8.5–9.0 with 2 N sodium hydroxide then treated with acetone (400 ml) and sodium hydrogen carbonate (100 g), cooled to −17°±2°. The reaction mixture was stirred for 45 minutes, treated with charcoal (20 g), filtered through celite, washed through with 50% aqueous acetone (3×80 ml) then the filtrate diluted with water (800 ml) and washed with ether (600 ml, 300 ml). The aqueous solution was covered with ether (600 ml), acidified to pH 2.0 with 2 N hydrochloric acid with vigorous stirring then the layers separated. The aqueous phase was extracted with ether (200 ml) then the combined ether extracts washed with a mixture of water (320 ml) and saturated brine (80 ml) then with saturated brine (2×400 ml) and dried over anhydrous magnesium sulphate.

The ether was removed in vacuo to give the free acid as a foam which was dissolved in fresh ether (3 l) and treated with 2 M sodium 2-ethylhexanoate in 4-methylpentan-2-one (200 ml, 0.40 mole). The suspension was diluted with more ether (1 l) then the solid collected, washed with ether and dried in vacuo over phosphorus pentoxide, 149 g, 75% yield, $\nu_{max}$ (KBr) 1765, 1680, 1607, 1460, 775 and 750 cm$^{-1}$, $\delta$ (D$_2$O) 1.47 (6H, s, 2×2CH$_3$), 1.80 (3H, s, Ar.CH$_3$), 4.27 (1H, s, 3H), 5.55 (2H, s, 5 and 6H), 6.8–7.5 (7H, m, thienyl and C$_6$H$_4$).

EXAMPLE 2

Sodium 6,β-[2-(2-methylphenoxycarbonyl]-2-thien-3'-ylacetamido]penicillanate Disodium ticarcillin (4.3 g, 100 mmole) in water (50 ml) was covered with ethyl acetate (30 ml) and acidified to pH 2.0 with 40% phosphoric acid. The ethyl acetate was separated, the aqueous phase extracted with further ethyl acetate (20 ml) then the extracts washed with water (50 ml) and brine (20 ml), dried and evaporated to a foam (4.12 g).

This ticarcillin diacid in ethyl acetate (20 ml) was cooled in an ice bath and treated with 2-methylphenol (1.19 g, 11 mmole) followed by dicyclohexylcarbodiimide (2.47 g, 12 mmole) then the mixture was stirred at room temperature overnight. The precipitated dicyclohexyl urea was filtered off, washed with ethyl acetate (10 ml), and the filtrate extracted with dilute sodium bicarbonate solution (2×25 ml) and water (20 ml). The aqueous solution was washed with ether (2×20 ml), acidified to pH 3.7 with 40% phosphoric acid and extracted with ether (3×20 ml). The extracts were washed with water (2×50 ml) and brine (20 ml), dried and evaporated to a foam (2.71 g).

The foam in fresh ether (50 ml) was treated with 2 N sodium 2-ethylhexonoate in 4-methylpentan-2-one (2.85 ml) and the precipitated sodium salt collected, washed with ether and dried in vacuo to give the title compound, 2.59 g, 52.2%, $\nu_{max}$ (KBr) 1765, 1675, 1605, 1460, 775 and 750 cm$^{-1}$, $\delta$ [(CD$_3$)$_2$SO] 1.48, 1.57 (6H, 2×s, 2×2CH$_3$), 2.08 (3H, s, ArCH$_3$), 3.96 (1H, s, 3H), 5.3–5.6 (3H, m, CHCONH, 5 and 6 H), 6.9–7.6 (7H, m, thienyl and C$_6$H$_4$), 9.0–9.3 (1H, m, CONH).

EXAMPLE 3

Preparation of oral dosage units in the form of a tablet (a) Sodium 6,β-[2-(2-methylphenoxycarbonyl)-2-thien-3'-ylacetamido]penicillanate as sole therapeutic agent Ingredients:

| | | mg |
|---|---|---|
| 1. | Sodium 6,β-[2-(2-methylphenoxycarbonyl)-2-thien-3'-ylacetamido]penicillanate | 494 (free acid) |
| 2. | Carboxymethyl sodium starch glycollate | 15 |
| 3. | Magnesium stearate | 12 |
| 4. | Microcrystalline cellulose | to 750 |

Items 1, 2 and 4 are blended with two thirds of item 3, and compressed on a rotary tablet machine. The slugs produced are milled, and the milled material blended with the remainder of item 3. The mixture is then compressed on a rotary tablet machine to form the final tablets.

(b) Sodium 6,β-[2-(2-methylphenoxycarbonyl)-2-thien-3'-ylacetamido]penicillanate and potassium clavulanate Ingredients:

| | | mg |
|---|---|---|
| 1. | Sodium 6,β-[2-(2-methylphenoxycarbonyl)-2-thien-3'-ylacetamido]penicillanate | 494 (free acid) |
| 2. | Potassium clavulanate | 100 (free acid) |
| 3. | Carboxymethyl sodium starch glycollate | 15 |
| 4. | Magnesium stearate | 12 |
| 5. | Microcrystalline cellulose | to 850 |

Tablets are prepared as in Example 3(a), both active ingredients being incorporated in the first stage slugging operation.

The tablets from Example 3(a) or 3(b) may be uncoated or a conventional film coating may be applied.

What is claimed is:

1. 6β-[2-(2'-methylphenoxycarbonyl)-2-thien-3'-ylacetamido]penicillanic acid of formula (II):

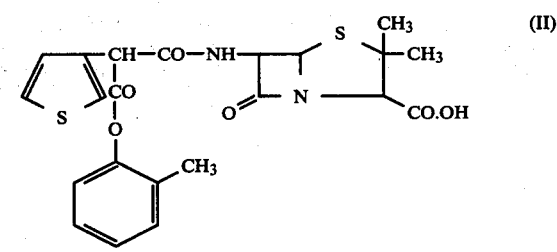

or a pharmaceutically acceptable salt or in vivo hydrolysable ester thereof.

2. Sodium 6,β-[2-(2'-methylphenoxycarbonyl)-2-thien-3'-ylacetamido]penicillanate.

3. An antibacterial pharmaceutical composition comprising an antibacterially effective amount of a penicillin as claimed in claim 1 together with a pharmaceutically acceptable carrier or excipient.

4. An antibacterial pharmaceutical composition comprising an antibacterially effective amount of a penicillin as claimed in claim 1 and a compound of formula (IX) or a pharmaceutically acceptable salt or ester thereof:

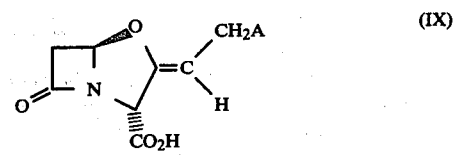

wherein
A is hydroxyl, substituted hydroxyl, thio, substituted thiol amino, mono- or di-hydrocarbylsubstituted amino, or mono- or di-acylamino.

5. An antibacterial composition of claim 3 which further comprises clavulanic acid or an alkali metal salt thereof.

6. An antibacterial composition as claimed in claim 5 wherein the penicillin is sodium 6β-[2-(2'-methylphenoxycarbonyl)-2-thien-3'-ylacetamido]penicillanate and the clavulanic acid alkali metal salt is potassium clavulanate.

7. An orally administrable antibacterial composition of enhanced bioavailability and absorption upon oral administration which comprises an antibacterially effective amount of the α-ortho-tolyl ester of α-carboxy-3-thienyl methyl penicillin together with a pharmaceutically acceptable carrier.

8. An orally administrable antibacterial composition according to claim 7 which further comprises an alkali metal salt of clavulanic acid.

* * * * *